United States Patent [19]
Bett et al.

[11] Patent Number: 5,313,821
[45] Date of Patent: May 24, 1994

[54] UNIFORM AND QUANTITATIVE EVALUATION OF AROMA EMITTING SUBSTANCES

[75] Inventors: Karen L. Bett, Kenner; Peter B. Johnsen, Metairie, both of La.

[73] Assignee: The United States of America, as represented by the Secretary of Agriculture, Washington, D.C.

[21] Appl. No.: 758,068

[22] Filed: Sep. 12, 1991

[51] Int. Cl.$^5$ .................... G01N 1/22; G01N 33/02
[52] U.S. Cl. ...................... 73/23.34; 73/863.23; 73/865.7
[58] Field of Search .............. 73/865.7, 866, 23.34, 73/863.23

[56] References Cited

U.S. PATENT DOCUMENTS

| | | | |
|---|---|---|---|
| 2,136,844 | 11/1938 | Fair et al. | 73/23.34 |
| 2,327,060 | 8/1943 | Pollak et al. | 73/23.34 |
| 2,837,912 | 6/1958 | Moncrieff | 73/865.7 |
| 3,618,359 | 11/1971 | Randebrock et al. | 73/23.34 |
| 3,636,772 | 1/1972 | Bennett | 73/866 |
| 3,902,851 | 9/1975 | Dravnieks | 73/23.34 |
| 4,022,054 | 5/1977 | Biederman | 73/23.34 |
| 4,235,098 | 11/1980 | Tisch | 73/863.23 |
| 4,247,298 | 1/1981 | Rippie | 73/866 |
| 4,249,655 | 2/1981 | Patureau et al. | 73/863.23 |
| 4,350,507 | 9/1982 | Greenough et al. | 73/863.23 |
| 4,382,808 | 5/1983 | Van Wormer, Jr. et al. | 73/863.23 |
| 4,411,156 | 10/1983 | Lowe | 73/866 |
| 4,456,014 | 6/1984 | Buck et al. | 73/863.23 |
| 4,461,184 | 7/1984 | Gandhi et al. | 73/863.23 |
| 4,961,916 | 10/1990 | Lesage et al. | 73/863.23 |
| 5,001,463 | 3/1991 | Hamburger | 73/863.23 |

FOREIGN PATENT DOCUMENTS

| | | | |
|---|---|---|---|
| 0017339 | 2/1983 | Japan | 73/866 |
| 0299752 | 12/1987 | Japan | 73/865.7 |
| 0022550 | 1/1990 | Japan | 73/23.34 |
| 2-272361 | 11/1990 | Japan | 73/865.7 |

Primary Examiner—Hezron E. Williams
Assistant Examiner—George M. Dombroske
Attorney, Agent, or Firm—M. Howard Silverstein; John D. Fado; Joseph A. Lipovsky

[57] ABSTRACT

The present invention is drawn to evaluation of the aroma of aroma-emitting substances, such as agricultural grains and oil seeds, in a safe and quantitative way. This is accomplished by causing a known volume of non-toxic gas to pass through the aroma-emitting substance, absorb the aroma, and deliver it to an evaluator. This enables the evaluator to sniff the aroma and thereby make gross quantitative evaluations with respect to the strength of any particular odor of the substance.

23 Claims, 4 Drawing Sheets

UNIFORM AND QUANTITATIVE EVALUATION OF AROMA EMITTING SUBSTANCES

FIELD OF THE INVENTION

The present invention relates to apparatus and methods wherein predetermined uniform volumes of non-toxic gas are passed through an aroma-emitting substance, such as a sample of agricultural grain or oil seed. The gas becomes laden with aroma from the substance and is delivered to an operative for evaluation by sniffing. The aroma-laden gas is preferably filtered to prevent potentially harmful substances, such as dust, mold, biotoxins, and spores, from being sniffed into the respiratory system of the operative.

BACKGROUND OF THE INVENTION

It is customary to evaluate various aroma-emitting solid substances by sniffing the aroma and making a judgement as to its quality. The evaluation can often be used to help establish the quality of the substance and whether it meets certain specifications. For example, the evaluation of agriculture products, especially grains and oil seeds, is important because it helps establish the quality, or grade, of such products in commerce. This enables the purchaser of the product to negotiate a fair price for any given grade of agricultural product, in consideration with other market forces. A major aspect to overall grading of agricultural products, such as grains and oil seeds, involves the evaluation of the aroma associated with the substance. The aroma of the grain or oil seed is typically evaluated for malodors which indicate such things as contamination by microorganisms, fumigants, insects, or any other agent which would degrade the grain or oil seed. Fumigant odors are typically picked-up in warehouse storage where fumigants are used to protect the grain and oil seed from pests. Other odors can be derived from shipping containers contaminated by the previous cargo.

The evaluation of aroma of agricultural grain and oil seed is presently done by an inspector placing his or her nose into a 3-cornered pan containing about 2 to 3 inches of grain or oil seed. When the inspector sniffs the aroma, it is often accompanied by undesirable and potentially harmful substances, such as dust, mold, spores, biotoxins, fungus, and comminuted grain particles. While some attempts have been made to improve on this technique, they have not met with widespread acceptance, primarily because they have been less effective for evaluating the aroma than the above conventional method. For example, a device know as the "Cargill Sniffer" was developed for evaluating aroma from substances such as grains and oil seeds. The "Cargill Sniffer" consists of a nose-cup on the end of a plastic tube about 6 to 9 inches long. The tube is placed in the grain and the inspector places his or her nose in the nose-cup and sniffs. The "Cargill Sniffer" proved to be too ineffective for accurate evaluation of grain aroma because it was difficult for the inspector to sniff enough aroma, in acceptable concentrations, to make accurate multiple evaluations, especially with respect to quantitative aspects. That is, multiple evaluations as to whether a particular odor encompassed in the overall aroma was weak, moderate, or strong.

Consequently, there still exists a need in the art for a device for the uniform evaluation of aroma from aroma-emitting substances, such as grains and oil seeds, which is capable of enabling the operative, or evaluator, to make a quantitative, as well as a qualitative judgement. There is also a need in the art for a device which can deliver an aroma sample substantially free of potentially harmful substances.

SUMMARY OF THE INVENTION

In accordance with the present invention, there is provided a sampling device for containing a sample of aroma-emitting substance, which device comprises:

(a) a container means provided with: (i) a cavity of sufficient size to contain a sample of the aroma-emitting substance; (ii) a sealable opening of sufficient size to permit said sample to pass into said cavity; (iii) an inlet of sufficient size to permit entry of a carrier gas, wherein said inlet is positioned at a point on said container means such that it directs said carrier gas through said sample, and wherein said inlet is sealingly connectable (i.e. attachable) to a gas delivery means; and (iv) an outlet of sufficient size to permit said carrier gas which passes through said aroma-emitting substance, to exit said cavity; and one or both of the following:

(b) a gas directing means operably attached to said outlet for directing said carrier gas passing through said outlet to a predetermined location outside of said container means; and/or (c) a filtering means attached to said container means at a position extending across said outlet so that said carrier gas passes through said filtering means prior to passing outside of the sampling device, wherein said filtering means defines effective pore size(s) which allow the carrier gas to pass through, but not impurities such as molds, spores, biotoxins, fungus, or dust.

In preferred embodiments of the present invention, the aroma-emitting substance is an agricultural grain or oil seed, and the carrier gas is air, and a screening means is provided inside of said container means and is positioned across said inlet to prevent the sample from entering the inlet.

In other preferred embodiments of the present invention, the inlet end of said container means is attached to a gas delivery means which is capable of delivering predetermined uniform volumes of carrier gas.

In yet other preferred embodiments of the present invention, gas delivery means includes a handheld piston pump and the gas directing means is a nose-cup.

In still other preferred embodiments of the present invention, the filtering means contains an exchangeable or cleanable filtering element, and at least a portion of the device is manufactured from a non-odorous material such as a stainless steel, a polycarbonate, or glass.

There is also provided, in accordance with the present invention, a method for evaluating the aroma of an aroma-emitting substance comprising the steps of:

(a) placing a sample of aroma-emitting substance in a container means provided with: (i) a cavity of sufficient size to contain the sample of the aroma-emitting substance; (ii) a sealable opening means of sufficient size to permit said sample to pass into said cavity; (iii) an inlet of sufficient size to permit entry of a carrier gas, wherein said inlet is positioned at a point on said container means such that said inlet directs said carrier gas through said sample, and wherein said inlet is sealingly connected to a source of carrier gas; and, (iv) an outlet of sufficient size to permit said carrier gas which passes through said aroma-emitting substance, to exit said cavity;

(b) flowing a predetermined volume of carrier gas from said source of carrier gas, through the inlet of said container means, through said sample of aroma-emitting substance, thereby becoming laden with said aroma, and through said outlet; and (c) sniffing said aroma-laden carrier gas.

DETAILED DESCRIPTION OF THE INVENTION

Figure 1:
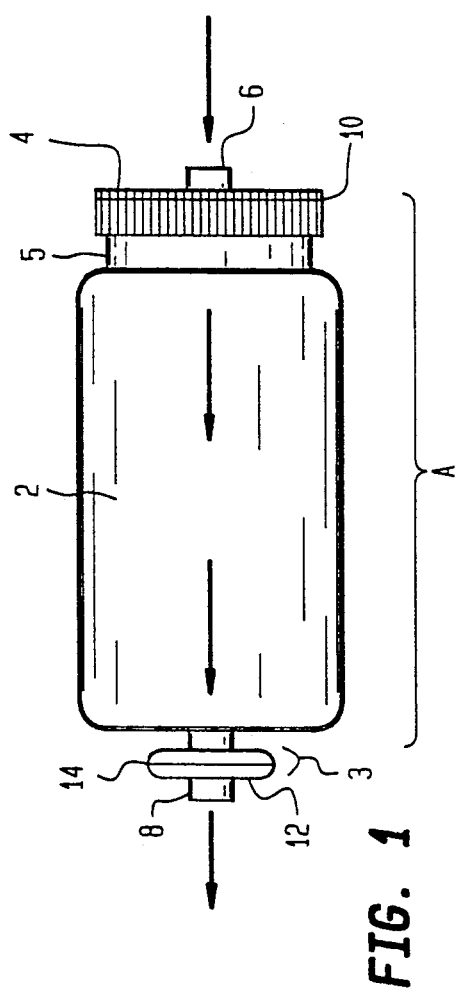
FIG. 1 is a side view of a sampling device of the present invention which shows a container means having an inlet which is sealingly attachable to a source of carrier gas and an outlet which contains a filtering means.

The present invention can be used to evaluate the aroma from any suitable aroma-emitting substance, preferably agricultural commodities and products, in a safe and quantitative manner. Such products include grains, oil seeds, as well as finished products, such as baked goods. Non-limiting examples of grains and oil seeds which may be evaluated in accordance with the sampling device of the present invention include soybeans, wheat, corn, barley, sorghum, flax seed, oats, rye, sunflower seed, triticale, rice, cotton seed, peanuts, and the like. The aroma of such a substance is often an indication of its quality and freshness. For example, premium agricultural grains and oil seeds will be free of all noxious and undesirable odors, also referred to as mal-odors. Such noxious and undesirable odors, which indicate a product of reduced grade, include mold, fungus, biotoxins, and spores, as well as various other contaminants such as oil and fumigants which can be acquired during shipping and storage. The aroma of agricultural grains and oil seeds can be evaluated in accordance with standards established by the United States Department of Agriculture in *Grain Inspection Handbook, Book II Grain Grading Procedures,* Federal Grain Inspection Service; May 1, 1988. An inspector will typically evaluate aroma from samples of agricultural grains and oil seeds by first placing a sample of grain or oil seed into a 3 cornered pan. The inspector then exhales; places his or her nose to, or sometimes into, the sample; then takes a series of relatively short sniffs until the lungs are filled. Of course, throughout the sniffing procedure the inspector is evaluating the odors that compose the overall aroma. Such a method: (a) does not prevent the inspector from inhaling potentially harmful substances which are present in the sample; and (b) makes it difficult for the inspector to make a series of quantitative evaluations as to the strength of any particular odor of the sample.

The present invention not only allows for a controlled volume of carrier gas to pass through the sample, but it also allows for the gas, which becomes laden with aroma from the sample, to be filtered as it passes out of the sampling device. That is, a predetermined volume of carrier gas, preferably deodorized air, is passed through the sample. The carrier gas becomes laden with the aroma of the sample and is preferably passed through a filtering means before exiting the device. By the carrier gas becoming laden with aroma, we mean that the carrier gas picks up, or absorbs, some of the aroma of the substance. It does not mean that it picks up any particular amount, or that it becomes saturated with the aroma. Thus, the term "carrier gas" is used to describe the gas which picks-up the aroma of the sample and carries it out of the sampling device. As previously mentioned, the filtering means serves the important function of filtering out such undesirable or potentially harmful substances as dust, mold, spores, fungus, biotoxins, and the like.

The use of a set volume of carrier gas, and set volume of sample, will enhance the uniformity of grain evaluations. That is, an operative using the device of the present invention can now make a series of quantitative evaluations of a particular component, or odor, of the sample. That is, whether a particular odor of the sample is weak, moderate, strong, etc.

Turning now to FIG. 1 hereof, a preferred sampling device is shown which is comprised of a container means A and a filtering means 3. The container means has an inlet end and an outlet end, as indicated by the arrows, and is provided with: (i) a cavity 2 of sufficient capacity to contain a sample of aroma-emitting substance for evaluation; (ii) a sealable opening, which for purposes of the FIG. 1 is an opening 5 with a removable cap 4, to permit said sample to be loaded into and unloaded out of the cavity; (iii) an inlet 6 having an orifice of sufficient size to permit the entry of a carrier gas, which inlet is also of a design which can be sealingly attached to a carrier gas source, or gas delivery means; and (iv) an outlet 8 having an orifice of sufficient size to permit said carrier gas, which becomes laden with aroma from a sample of aroma-emitting substance, to pass from the cavity. The capacity of the cavity of the container means will typically be from about 0.1 to 1 liter. Also, the removable cap 4 may be of any appropriate design, including a screw type or bayonet type. There is also preferably provided a screening means 10 positioned such that it lies across the inlet. It need not necessarily be contained in the removable cap 4 as shown in this FIG. 1, but it can be anywhere between the sample and the orifice of the inlet. The screening means is of sufficient permeability to allow passage of the carrier gas into the cavity but which will prevent any sample from exiting the cavity through the orifice of said inlet. The screening means can be constructed out of any appropriate material, such as a polymeric material or a metallic material.

The filtering means 3 is provided to prevent the passage of potentially harmful substances such as molds, spores, fungus, biotoxins, and dust, with the aroma-laden carrier gas. The filtering means shown in this figure comprises a housing 12, which houses a filtering element 14, which is positioned across the outlet so that the aroma-laden carrier gas must filter through it as it exits the container means. The filtering element is of an effective pore size to allow the passage of the aroma-laden gas but not the passage of potentially harmful substances as previously mentioned. Of course, the precise size of the filter pores will depend on the smallest particle one wishes to filter and still allow for an acceptable flow of aroma-laden gas through the filtering means. Generally, the diameter of the pores of the filtering means will be from about 0.1 to 1 microns, preferably about 0.15 to 0.75 microns, more preferably about 0.2 to 0.5 microns, and most preferably about 0.2 to 0.4 microns.

Figure 2:
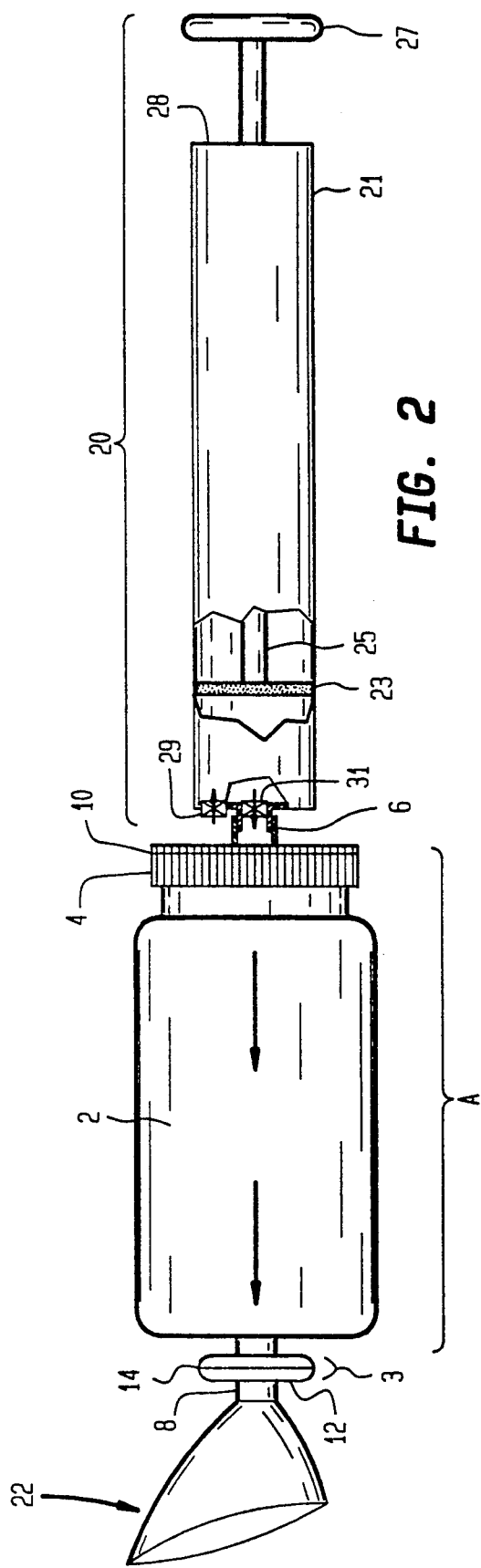
FIG. 2 is a partially cut-away side view of a preferred embodiment of the sampling device of the present invention which also shows: (a) a gas directing means in the form of a nose-cup attached downstream of the filtering means; and (b) a mechanical hand operated piston pump as the carrier gas delivery means.
Figure 3:
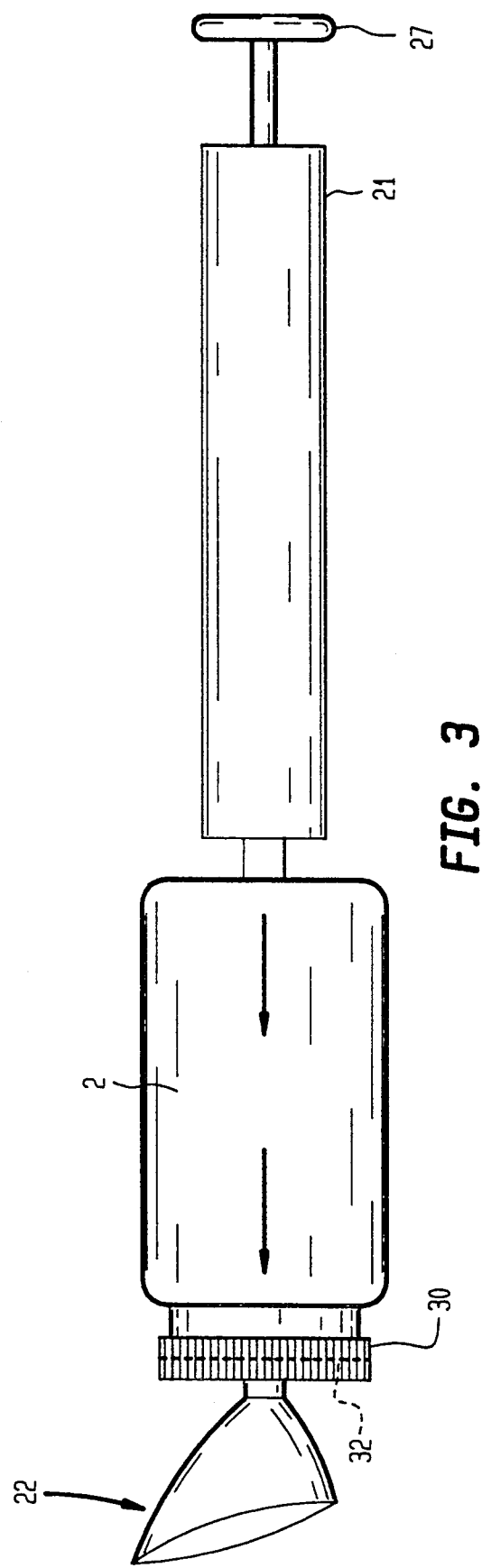
FIG. 3 is a side view of another preferred embodiment of a sampling device of the present invention which shows an alternative filtering means comprised of a filtering element contained in a filter compartment located within a removable cap.
Figure 4:
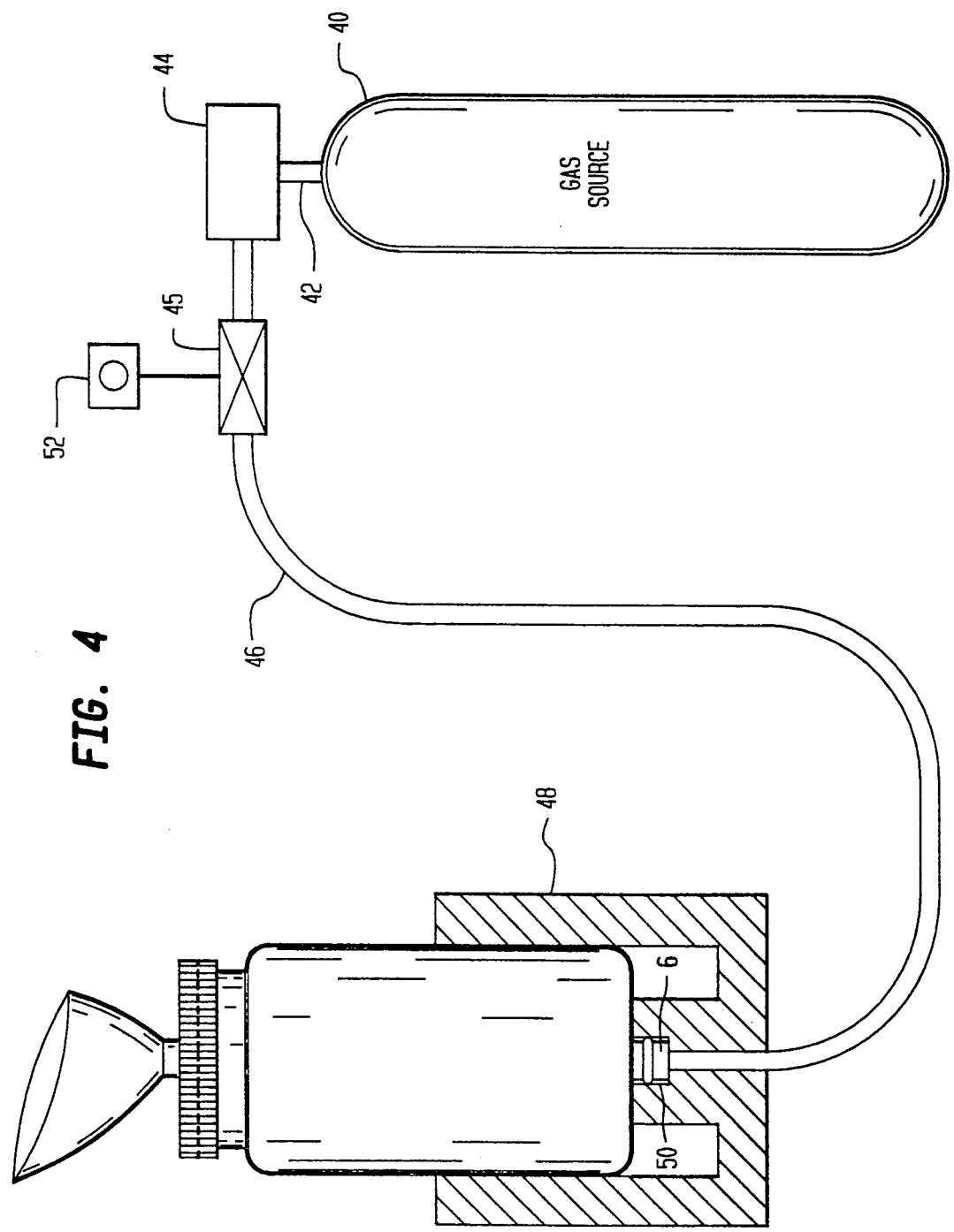
FIG. 4 is a schematic representation of yet another embodiment of the sampling device of the present invention which shows an alternative carrier gas delivery means including a tank of compressed carrier gas. The delivery of a predetermined volume of carrier gas is controlled by a valve which may be activated by a foot or hand switch.

FIG. 2 hereof shows a sampling device of the present invention connected to a source of carrier gas, or carrier gas delivery means which is capable of delivering an effective breathable volume of gas at an effective evaluation rate. That is, by effective breathable volume, is meant that an average normal operative will be able to breath substantially the entire volume of gas into his or her lungs. By, effective evaluation rate, is meant that the rate is a rate at which an operative can effectively evaluate the aroma. That is, if the rate is too fast or too slow, the operative will not be able to distinguish all of the components, or odors, of the sample. Such an effective rate will typically be from about 0.5 to 5 seconds, preferably from about 1 to 2 seconds.

The gas delivery means, or carrier gas source, can be any suitable means for delivering such volumes at such rates. Non-limiting examples of such gas sources include: hand operated piston and diaphragm pumps; sources of compressed carrier gas, such as a cylinder of compressed gas, an air compressor with a holding tank; and air pumps. Also suitable is a bellows type of device (illustrated in FIG. 5 hereof) which is capable of delivering a predetermined volume of air. The delivery of the carrier gas from compressed gas sources can be regulated by any suitable means, such as a standard gas regulator or gas flow meter. The gas delivery means shown in FIG. 2 is a hand operated piston pump 20. It will be noticed that the terms "gas delivery means" and "source of carrier gas" are sometimes used interchangeably throughout this specification. The hand operated piston pump is comprised of a cylinder 21, a piston 23 in sealing contact with the interior wall of the cylinder and connected to an end rod 25. It is preferred that the handle end of the cylinder contain an annular end cap 28 having a centered hole so that the end rod can pass back and forth through it. At the other end of said rod is a handle 27. There is also provided check valve 29 for letting air into the cylinder but not out, and check valve 31 for letting air out of, and not into, said cylinder.

The sampling device of FIG. 2 is also provided with a gas directing means 22 for directing the aroma-laden carrier gas to a restricted area outside of the container means. The gas directing means can be referred to as a nose cup which substantially conforms to the upper lip and nose area of an operative for directing substantially all of the aroma-laden carrier gas to the nostril area of the operative.

The sampling device of FIG. 2 is used by removing cap 4 and placing a sample of aroma-emitting substance into cavity 2 of the container means. The cap is then sealingly secured to the container means whereupon the device is held substantially vertical by placing the gas directing means 22 in the vicinity of the nose of an operative standing in an upright position. The operative then draws back on handle 27 thereby pulling piston 23 away from the container means end and toward the handle end of the cylinder. By doing so, the air, is drawn into the cylinder through check valve 29. When the piston reaches a predetermined distance down the cylinder, usually the entire length of the cylinder, the operative pushes the handle back toward the container means, thus causing the piston to push the air out of the cylinder and through check valve 31, through inlet 6, and through the sample of the aroma-emitting substance. While passing through the aroma-emitting substance, the gas picks up aroma from the substance. This is referred to herein as becoming aroma-laden. The aroma-laden air then passes out of the container means by passing through outlet 8, through filtering means 3 and is directed to the vicinity of the operative's nose by gas directing means 22. An alternative type of piston pump would be one that does not contain check valves so that the air is passed through the sample twice. That is, one time when the handle is pulled back, thereby causing air to pass through the sample and into the pump cylinder, and another time when the handle is pushed inward, thereby causing the air to leave the pump cylinder and through the sample and out the sampling device.

FIG. 3 hereof shows a sampling device of the present invention similar to that of FIG. 2 but having an alternative combination cap and filtering means 30. The filtering means in this figure is a filtering element 32 positioned in the cap and across the outlet.

FIG. 4 hereof is another type of sampling device system of the present invention wherein a carrier gas source 40 is shown, which can be a tank of non-toxic compressed gas, such as air; an air pump; an air compressor; or any other suitable source. In this figure, the gas source is shown as a tank of compressed gas. The gas leaves the gas source by way of line 42 to pressure regulating means 44. The pressure regulating means can be any which is appropriate for delivering the volumes of gas at the pressures required for proper use of the sampling device. Typically, the pressure regulating means will be a standard gas pressure regulator for controlling the outlet pressure of the compressed gas source. Either single stage or double stage regulators may be used, although double stage regulators are capable of more sensitive outlet pressure control. Such pressure regulators are well known in the art and a more detailed description is not needed herein. Such regulators and their principle of operation can be found in *Handbook of Compressed Gases,* Compressed Gas Association, Inc., Van Nostrand Reinhold Company, 1981.

The carrier gas leaves the pressure regulator under controlled reduced pressure via line 46 and passes through valve 45 on the way to inlet 6 of the sampling device. The sampling device is the same as that described in FIG. 2 hereof. The sampling device is shown in a holding means 48 which is provided with a connecting means 50 for sealingly accepting the inlet of the sampling device.

The flow of gas from the gas source to the sampling device is controlled by valve 45 which is preferably a solenoid type of valve electrically controlled by switch 52, which is preferably activated by the foot or hand of the operative. The valve will be normally closed and when the operative activates the switch, the valve opens and lets gas flow to the sampling device. The valve can be such that as long as the operative holds the switch in an activating position, the valve will remain open. Because it is preferred that substantially the same volume of gas be passed through each sample for comparison purposes, an automatic timing means should be used. That is, when the operative activates the switch, a timing means, preferably electrical, is activated so that it holds the valve open for a predetermined amount of time. In this way, the operative can merely load a sample of aroma-emitting substance into the container means, place it into the holding means 48, which is in fluid contact with the carrier gas source, and actuate the gas source with his or her foot or hand. This will allow for multiple evaluations to be made on the sample in a shorter period of time than the sampling device systems of FIGS. 2 and 3 hereof. The holding means 48 can be of any suitable design for the convenience of the operative. For example, it can sit on a table or bench, or it can be supported with legs.

Figure 5:
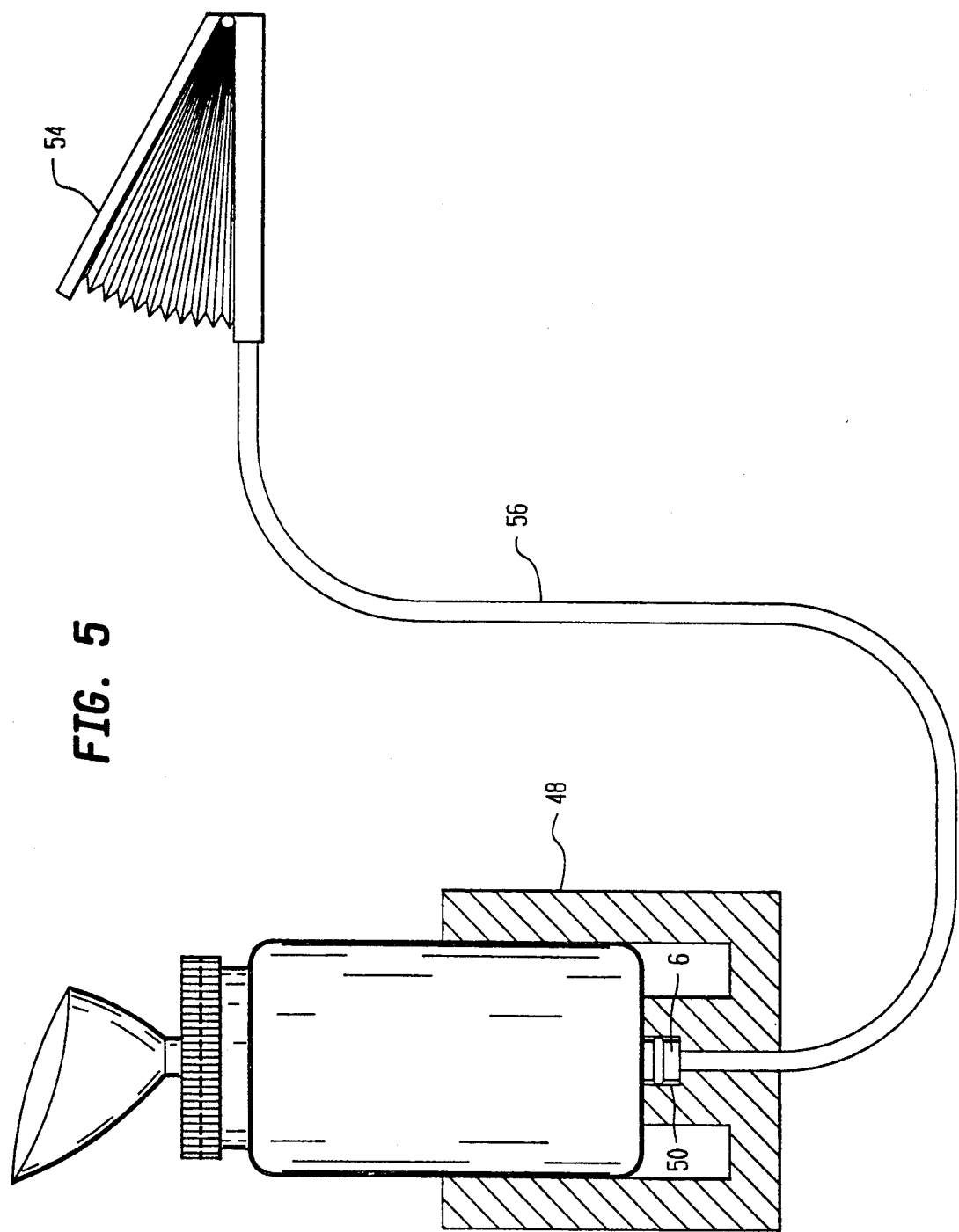
FIG. 5 is a representation of still another embodiment of the present invention in which the source of carrier gas is a foot operated bellows device.

FIG. 5 hereof is yet another embodiment of the present invention which shows another alternative gas delivery means. The gas delivery means in FIG. 5 is a foot operated bellows 54 fluidly connected via line 56 to the inlet of the container means.

Materials which can be used for the manufacture of any one or more of the parts of the sampling device of the present invention are preferably those materials which will not add odors to the aroma laden gas. Non-limiting examples of such preferred material include those substantially odorless materials such as, stainless steels, polycarbonates, and glass. More preferred are stainless steels and polycarbonates, and most preferred are stainless steels.

Various changes and/or modifications, such as will present themselves to those familiar with the art may be made in the device of the present invention without departing from the spirit of the present invention, whose scope is commensurate with the following claims.

INDEX OF ELEMENTS DESIGNATED BY A SYMBOL

A container means
2 cavity
3 filtering means
4 removable cap
5 sealable opening
6 inlet
8 outlet
10 screening means
12 housing
14 filtering element
20 hand operated piston pump
21 cylinder
22 gas directing means
23 piston
25 end rod
27 handle
28 annular end cap
29 check valve
30 filtering means
31 check valve
32 filter element
40 carrier gas source
42 line
44 pressure regulating means
45 valve
46 line
48 holding means
50 connecting means
52 switch
54 bellows
56 line

What is claimed is:

1. A hand held sampling device for containing a sample of an aroma-emitting substance for evaluation of the aroma in a non-continuous manner, which device is comprised of:
   (a) a container means provided with: (i) a cavity of sufficient size to contain a sample of the aroma-emitting substance; (ii) a resealable opening of sufficient size to permit said sample to pass into said cavity; (iii) an inlet of sufficient size to permit entry of a carrier gas, wherein said inlet is positioned at a point on said container means such that it directs said carrier gas through said sample, and wherein said inlet is sealingly connectable to a gas delivery means; and (iv) an outlet of sufficient size to permit said carrier gas, to pass from said cavity; and
   (b) a filtering means positioned across said outlet so that said gas passes through said filtering means.

2. The sampling device of claim 1 wherein there is also provided a gas directing means operably attached to said outlet for directing said carrier gas passing through said outlet to a predetermined location outside of said container means.

3. The sampling device of claim 2 wherein said filtering means contains a filtering element selected from the group consisting of porous paper, porous polymeric material, and porous metallic material, wherein said filter element defines pores of a size large enough to allow passage of said carrier gas at a predetermined rate, but small enough to retain molds, biotoxins, spores, and dust particles.

4. The sampling device of claim 1 which is manufactured from a material selected from stainless steels, polycarbonates, and glass.

5. A hand-held sampling device for containing a sample of an aroma-emitting substance in a non-continuous manner, which device is comprised of:
   (a) a container means provided with: (i) a cavity of sufficient size to contain a sample of the aroma-emitting substance; (ii) a resealable opening of sufficient size to permit said sample to pass into said cavity; (iii) an inlet of sufficient size to permit entry of a carrier gas, wherein said inlet is positioned at a point on said container means such that it directs said carrier gas through said sample; and (iv) an outlet of sufficient size to permit said carrier gas to pass from said cavity; and
   (b) a filtering means positioned across said outlet so that said gas passes through said filtering means; and
   (c) carrier gas delivery means, operably attached to said inlet, for delivering a predetermined volume of said carrier gas through said inlet and sample, thereby becoming laden with aroma from said sample.

6. The sampling device of claim 5 further including a gas directing means operably attached to said outlet for directing said carrier gas passing through said outlet to a predetermined location outside of said container means.

7. The sampling device of claim 6 wherein said gas directing means is a nose cup.

8. The sampling device of claim 7 further including filtering means positioned across said outlet so that said gas passes through said filtering means.

9. The sampling device of claim 8 wherein said carrier gas delivery means includes a handheld piston pump.

10. The sampling device of claim 8 wherein said carrier gas delivery means includes a tank of compressed carrier gas.

11. The sampling device of claim 10 wherein said carrier gas delivery means includes a solenoid valve means with an operably associated electrical switch means for actuation of said solenoid valve means, and wherein said solenoid valve means is operable connected between said tank of compressed carrier gas and said inlet, for controlling flow of said carrier gas from said tank of compressed carrier gas to said inlet.

12. The sampling device of claim 8 in which said carrier gas delivery means includes a bellows in fluid communication with said container means.

13. The sampling device of claim 8 wherein said container means consists of a non-odorous material.

14. The sampling device of claim 13 wherein said non-odorous material is selected from the group consisting of stainless steels, polycarbonates, and glass.

15. A method for evaluating aroma odor intensity of an aroma-emitting substance in a non-continuous manner, comprising the steps of:
(a) placing a sample of aroma-emitting substance in a container means provided with: (i) a cavity of sufficient size to contain said sample of said aroma-emitting substance; (ii) a resealable opening of sufficient size to permit said sample to pass into said cavity; (iii) an inlet of sufficient size to permit entry of a carrier gas, wherein said inlet is positioned at a point on said container means such that inlet directs said carrier gas through said sample, and wherein said inlet is sealingly connected to a source of carrier gas; (iv) an outlet of sufficient size to permit said carrier gas which passes through said aroma-emitting sample, to pass from said cavity; and a filtering means positioned across said outlet so that said gas passes through said filtering means;
(b) flowing a predetermined volume of carrier gas from said source of carrier gas, through said inlet of said container means, through said sample of aroma-emitting substance thereby becoming laden with said aroma, and through said outlet; and
(c) sniffing said aroma-laden carrier gas.

16. The method of claim 15 further including the step of utilizing gas directing means, operably attached to said outlet, for directing said aroma-laden carrier gas passing through said outlet to a predetermined location outside of said container means.

17. The method of claim 16 wherein said gas directing means is a nose cup.

18. The method of claim 15 further including the step of employing filter means, positioned across said outlet, for filtering impurities from said aroma-laden carrier gas.

19. The method of claim 15 wherein said step of flowing includes, expelling said predetermined volume of carrier gas from a handheld piston pump through said inlet of said container means and through said sample.

20. The method of claim 15 wherein said step of flowing includes, permitting said predetermined volume of carrier gas to flow from a tank of compressed carrier gas through said inlet of said container means and through said sample.

21. The method of claim 15 wherein said step of flowing includes, expelling said predetermined volume of carrier gas from a bellows through said inlet of said container means and through said sample.

22. The method of claim 15 wherein said container means consists of a non-odorous material.

23. The method of claim 22 wherein said non-odorous material is selected from the group consisting of stainless steels, polycarbonates, and glass.

* * * * *